United States Patent

Kelly et al.

[11] Patent Number: 5,865,740
[45] Date of Patent: *Feb. 2, 1999

[54] ELECTRODELESS EKG SENSOR SHEET

[75] Inventors: Robert John Kelly, Camarillo; Thomas G. Lavine, Woodland Hills, both of Calif.

[73] Assignee: Unilead International, Inc., Orinda, Calif.

[ * ] Notice: The term of this patent shall not extend beyond the expiration date of Pat. No. 5,507,290.

[21] Appl. No.: 977,734

[22] Filed: Nov. 25, 1997

(Under 37 CFR 1.47)

Related U.S. Application Data

[63] Continuation of Ser. No. 631,214, Apr. 12, 1996, abandoned, which is a continuation of Ser. No. 265,767, Jun. 27, 1994, Pat. No. 5,507,290, which is a continuation of Ser. No. 82,809, Jun. 25, 1993, abandoned, which is a continuation of Ser. No. 541,718, Jun. 21, 1990, abandoned.

[51] Int. Cl.⁶ .................................. A61B 5/0402
[52] U.S. Cl. .................... 600/382; 600/389; 600/391; 600/393

[58] Field of Search ...................... 600/382, 386, 600/388, 389, 391, 392, 393

[56] References Cited

U.S. PATENT DOCUMENTS

| | | | |
|---|---|---|---|
| 4,102,331 | 7/1978 | Grayzel et al. | 128/640 |
| 4,353,372 | 10/1982 | Ayer | 128/640 |
| 4,583,549 | 4/1986 | Manoli | 128/640 |
| 4,674,511 | 6/1987 | Cartmell | 128/640 |
| 5,507,290 | 4/1996 | Kelly et al. | 128/640 |

FOREIGN PATENT DOCUMENTS

| | | | |
|---|---|---|---|
| 122258 | 2/1972 | Denmark | 128/641 |
| 0275811 | 7/1988 | European Pat. Off. | 128/640 |
| 2619300 | 2/1989 | France | 128/644 |

*Primary Examiner*—Lee Cohen
*Attorney, Agent, or Firm*—Fitzpatrick, Cella, Harper & Scinto

[57] ABSTRACT

The invention relates to an electrodeless device for administering an electrocardiogram consisting essentially of a single flexible sheet having multiple electrical strips or wires pre-positioned for placement on a patient's chest. The device includes at least two positioning means.

8 Claims, 3 Drawing Sheets

ELECTRODELESS EKG SENSOR SHEET

This application is a continuation of application Ser. No. 08/631,214, filed Apr. 12, 1996, now abandoned, which is a continuation of application Ser. No. 08/265,767, filed Jun. 27, 1994, now U.S. Pat. No. 5,507,290, which is a continuation of application Ser. No. 82,809, filed Jun. 25, 1993, which is a continuation of application Ser. No. 07/541,718, filed Jun. 21, 1990, now both abandoned.

FIELD OF THE INVENTION

This invention relates to low cost disposable devices for electrocardiographic monitoring and telemetry, and more particularly devices for interfacing between a patient and electrocardiography apparatus. More particularly, the invention concerns an electrocardiographic device which can be used without electrodes.

BACKGROUND OF THE INVENTION

Electrocardiographic monitoring and telemetry have been in use in the United States for some time for screening and diagnosis of cardiopathy. Electrocardiography provides a graphic registration, commonly known as an EKG, of movements of the heart using electrical signal sensing. In general, electrical leads used to transmit signals from the patient's cardiovascular system are fixed to the skin of the patient individually, at suitable locations, using suction cups and conductive adhesives to provide the necessary electrical connection for reading the heart movements through a patient's skin.

For screening and evaluation, the patient should be ambulatory so that readings can be taken during different degrees of physical exertion to demonstrate the reaction of the heart to differing stresses. A standard type of testing includes electrocardiographic monitoring of a patient during a set of standardized treadmill exercises. It is well recognized that this type of screening and evaluation are important for diagnosis of new ischemic cardiac episodes in the chronically symptomatic cardiac patient as well as the identification of "silent ischemic" periods of myocardial oxygen insufficiency not associated with classic chest pain. These ischemic electrocardiographic changes can be accurately recognized only if a full screen electrocardiogram is performed. The standard full screen electrocardiogram includes readings taken by electrically conductive leads at standard chest positions combined to provide readings.

Periodic electrocardiograms can provide a physician with a cardiographic profile of an individual patient for early detection and diagnosis of cardiovascular diseases. For purposes of providing an accurate profile, it is important that each electrocardiogram be taken with leads affixed about the same location on the patient. The accuracy of each electrocardiogram requires that the leads be accurately placed and that they remain fixed while the patient is ambulatory. In addition, to provide accurate information for an individual patient, a series of electrocardiograms are taken and compared to one another to detect changes in the reaction of the individual patient's heart to the same stresses. Therefore, it is important that placement of the leads be consistent from one electrocardiogram session to another.

As can be appreciated, accurately placing and securing a large number of leads can be difficult and time consuming. In addition, electrocardiograms are taken periodically and the results compared to one another to provide a continuing profile of an individual patient's heart movements for early diagnosis and treatment of heart disease and to identify "silent ischemic" periods of myocardial oxygen insufficiency in chronically symptomatic cardiac patients. It would therefore be advantageous to have a device for accurate placement of leads for accurately reproducing test conditions for comparison between testing episodes.

Although a full screen, twelve point electrocardiogram provides the most accurate picture for recognizing ischemic electrocardiographic changes, because of the time required to place and secure individual leads, electrocardiograms taken during an acute symptomatic episode of a cardiac patient are generally limited to two- to four-lead readings. It would therefore be advantageous to have a device which enables more leads to be accurately placed and secured quickly during an acute symptomatic episode.

U.S. Pat. No. 4,608,987 to H. E. Mills relates to a vest-like garment having a plurality of aperatures adapted for receiving electrodes. However, there is no provision to ensure that the electrodes are placed each time of reuse of the vest about the same location.

U.S. Pat. No. 4,583,549 to S. Manoli relates to an ECG electrode pad with a plurality of ECG electrodes which are repositioned with regard to each other and not with reference to their previous position.

U.S. Pat. No. 4,365,634 to Bare et al discloses a multi-terminal electrode construction having a pair of separate support members adapted for the transcutaneous application of an electrode to a patient. A multiterminal design is provided by a conductive pattern printed on a semiflexible sheet. The pattern is printed with conductive ink in a binder composition. However, there is no means provided which can ensure the reapplication of the terminals to the same location so as to obtain a better comparison of test results.

U.S. Pat. No. 4,593,698 to R. J. Athans discloses an electrocardiograph sensor positioning device for repeatedly positioning electrocardiograph sensors. The device establishes a longitudinal reference between two anatomical landmarks on an individual. A second reference path is then found and recorded. The recorded locations are necessary to ensure a similar location. One of the problems with the use of the device requires that the second examining physician have the information from the first physician in order to obtain readings at the same locations. The device of the invention provides uniform examination without requiring information from others on placement of the electrodes.

U.S Pat. No. 4,763,660 discloses a multilayer disposable electrode belt device which contains a plurality of flexible non-conductive layers. There is also provided anatomical placement reference means.

A vest provided with prearranged electrodes is shown in FIG. 4.

Telephonic units for transmitting ECG signals to ECG receiving equipment at a cardiologist's office are described generally in U.S. Pat. No. 3,910,260. Usually such transmission takes place in emergency vehicles where prior medical history may not be readily available. In order to obtain meaningful and reliable information repeatable ECG signals are necessary for the cardiologist. None of the prior art devices have provided a low cost solution to obtaining repeatable ECG signals in the field by untrained or non-professionals parties.

The present invention provides an easily manufactured accurate, repeatable placement of leads for electrocardiograms which is repeatable without knowledge of the previous locations. The device of this invention lowers the time involved in placement and affixation by providing a sensor sheet incorporating multiple leads which are preferably pre-wired to a terminus that can connect to a standard electrocardiographic cable or to a telemetric unit, as more fully discussed below.

SUMMARY OF THE INVENTION

In general, the present invention includes a low cost flexible single layered vest or bib. for electrically connecting a patient with an electrocardiographic monitoring device. The bib has incorporated therein electrical conducting strips or wires for transmitting electrical impulses from a patient to be monitored to the electrocardiograph device. The bib incorporates at least six, preferably 8–12, of the strips in a predetermined pattern corresponding to a standard, full screen electrocardiogram. The strips are used both as electrodes and as transmitters for the electrical impulses. The conventional sensory electrodes are optional since the apparatus can function effectively without them.

Each of the strips includes a first end mounted at predetermined positions on a patient's chest and a second end for connection with an electrocardiographic device.

More particularly, the present invention includes a single sheet non-conductive substrate, for example, a sheet of non-conductive natural or plastic material polyvinyl chloride, polyethylene polyphenylene, terephthalate, cotton, rayon, and the like, having incorporated therein a plurality of electrically conductive strips or wires. Each strip includes a first end portion or receptor end adapted for electrical connection with the skin of the patient for receiving electrical impulses. A second end of each strip terminates in a common electrical connector or cable junction on the sheet which is adapted for connection with a standard type of cable juncture for connection with the electrocardiograph device.

It is a feature of the invention to provide electrically conductive adhesive means pre-applied to the strips for assuring electrical contact with skin. One or more positioning members are included to facilitate positioning the bib in the proper location on the patient's chest to assure that each of the pre-positioned conductors or electrodes is located in appropriate overlying relationship for obtaining readings at selected locations on the patient's chest. The positioning members are advantageously located to overlie the easily recognizable bony chest landmarks of the patient, i.e. the clavicles and sternum. The positioning members are slots, notches, openings in the bib for locating by touch the sternum notch and the clavicle notch.

A standard pattern may be printed in any suitable manner on the bib to further facilitate positioning of the bib on the patient. The pattern includes an outline of the clavicles and sternum landmarks, or any other recognizable outline of the chest landmarks.

The conductive strips are printed on a single layered film or sheet by any conventional printing or silk screening type of process. The portion of the strip which need not be exposed can be coated with a non-conductive coating or adhesive material which can be cured.

It is therefore an object of the present invention to provide a method and apparatus which may repeatedly position a plurality of body electrodes about the same position on the body without knowledge of the prior-positioning.

It is a further object of the invention to provide a garment for supporting a plurality of electrocardiograph sensing strips which are set in a predetermined pattern that can be repeatedly placed on a patient's body about the same position for connection to electrocardiograph equipment.

It is still further object of the invention to provide a garment having a plurality of electrocardiograph sensing strips without electrodes which can be placed on a patient by untrained parties or the patient provides reliable and repeatable ECG signals.

Detailed Description of the Preferred Embodiment

Figure 1:
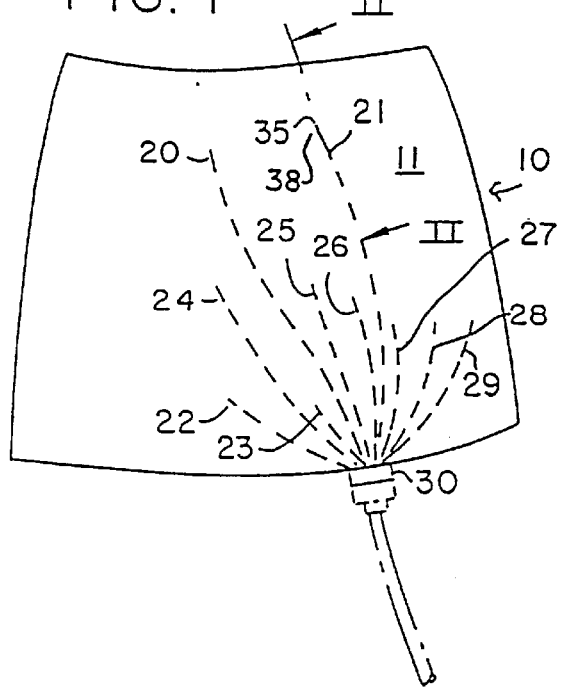
FIG. 1 is a front view of a preferred embodiment of the invention.

An illustrated in FIG. 1, a preferred embodiment of the electrode-less EKG sensor sheet of the instant invention includes a single layered flexible sheet or bib 10 having a contact surface 11 for placement on the chest region of a patient.

A plurality of electrically conductive strips are mounted on the bib 10 to transmit electrical impulses from the patient's chest to an electrocardiographic recording device. In the preferred embodiment illustrated in the drawing, with reference to FIG. 1, the strips are configured in the pattern normally used in the chest configuration for standard treadmill exercise testing. More particularly, the strips include the normal limb leads or strips for extremities such as a right arm strip 20, left arm strip 21, right leg strip 22, left leg strip 23 as well as the normal chest strips 24, 25, 26, 27, 28 and 29. The four limb strips alone can provide a standard two- or four-lead or strip electrocardiogram. The four limb strips when combined with the chest strips 24 and 25 in addition to the individual strips provide the standard type 12 lead electrocardiogram.

Figure 2:
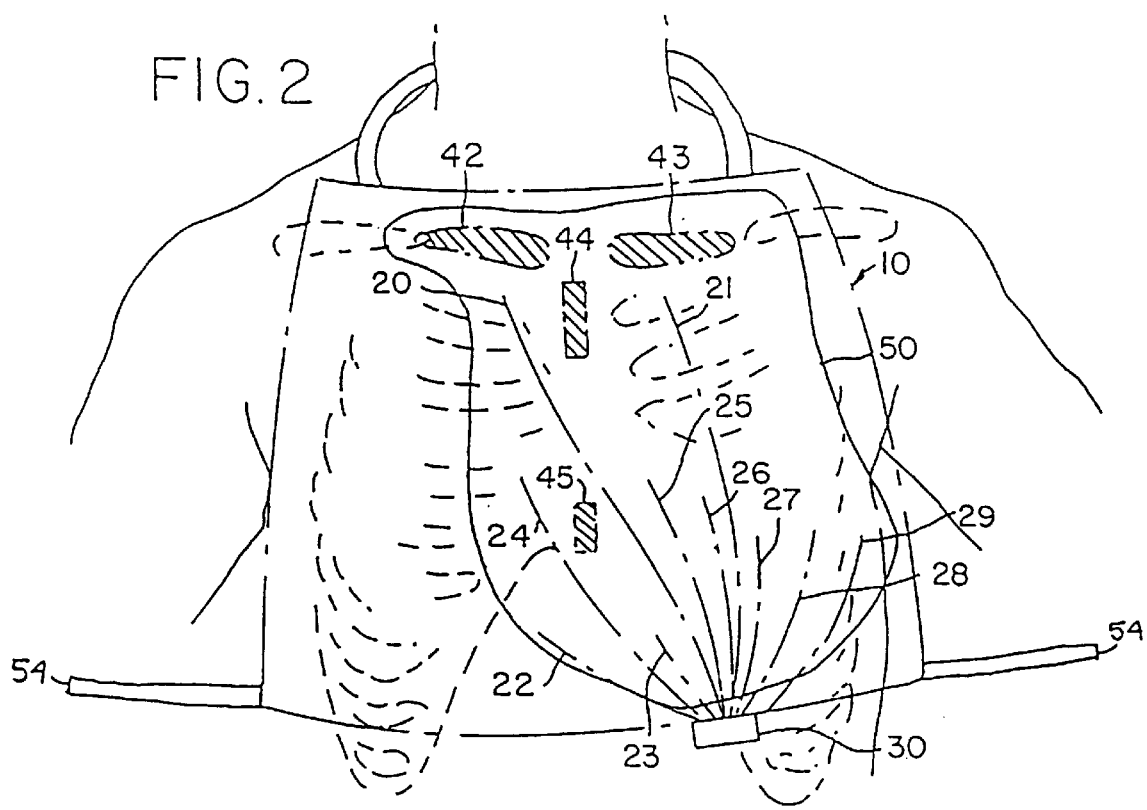
FIG. 2 is a view similar to FIG. 1, showing the preferred embodiment in phantom to illustrate placement of the sheet on a patient.

With reference to FIG. 2, the right arm strip 20 and the left arm strip 21 are located below the clavicles bilaterally. The right leg strip 22 and left leg strip 23 are located below the sternum. The chest strip 26 is located approximately at the mid-axillary line. Each of strips 20–29 is electrically connected at one end to a suitable connector such as cable junction 30 illustrated in FIGS. 1 and 2.

Each of the strips 20–29 includes an exposed receptor end, such as end 35 on the left arm strip 21. A conductive adhesive or gel 38 is preferably applied to the end 35 to assure good electrical contact with the patient's skin.

Figure 3:
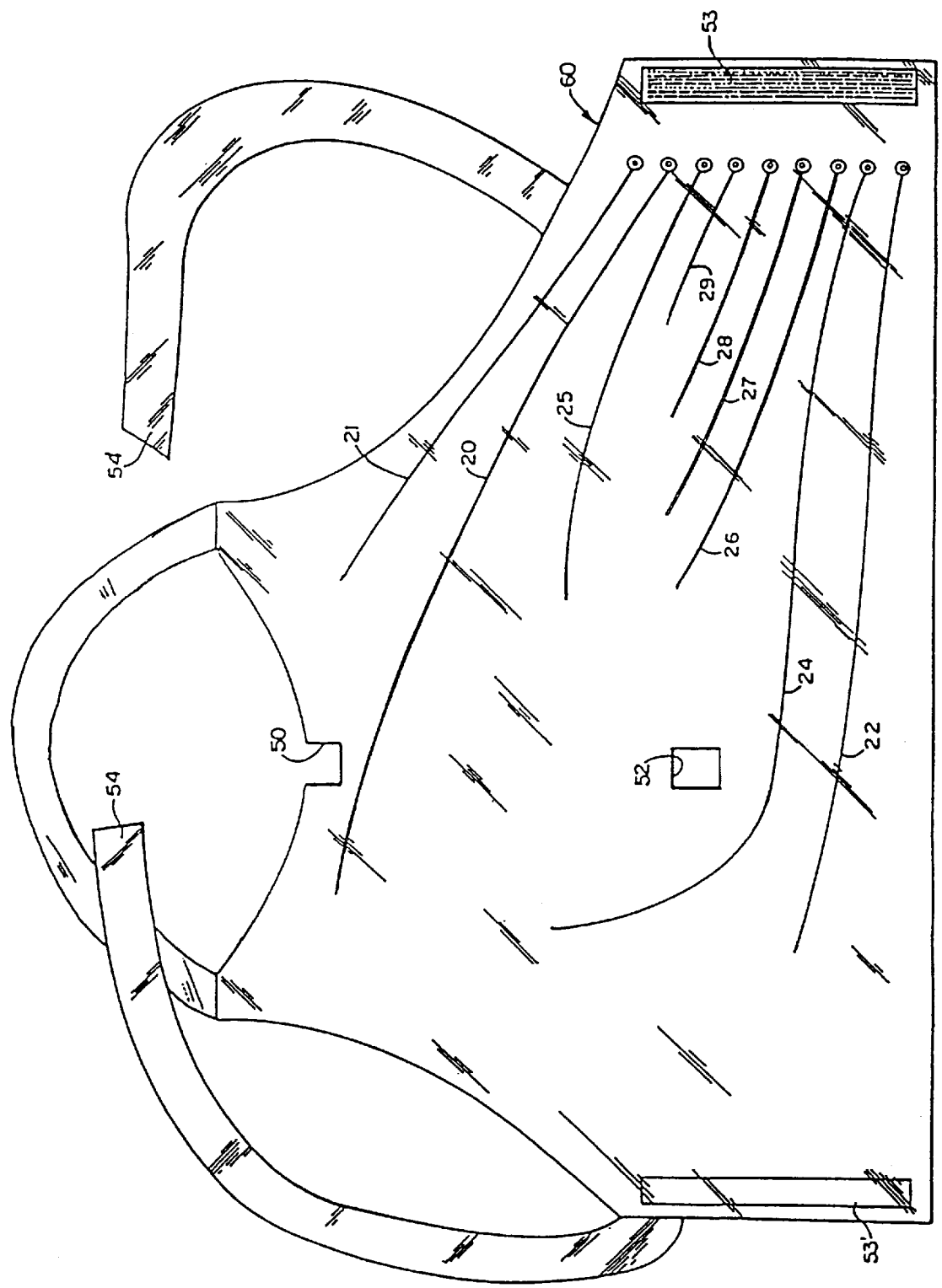
FIG. 3 is a similar to FIG. 2 and illustrates the sternum and clavicle positioning means.
Figure 4:
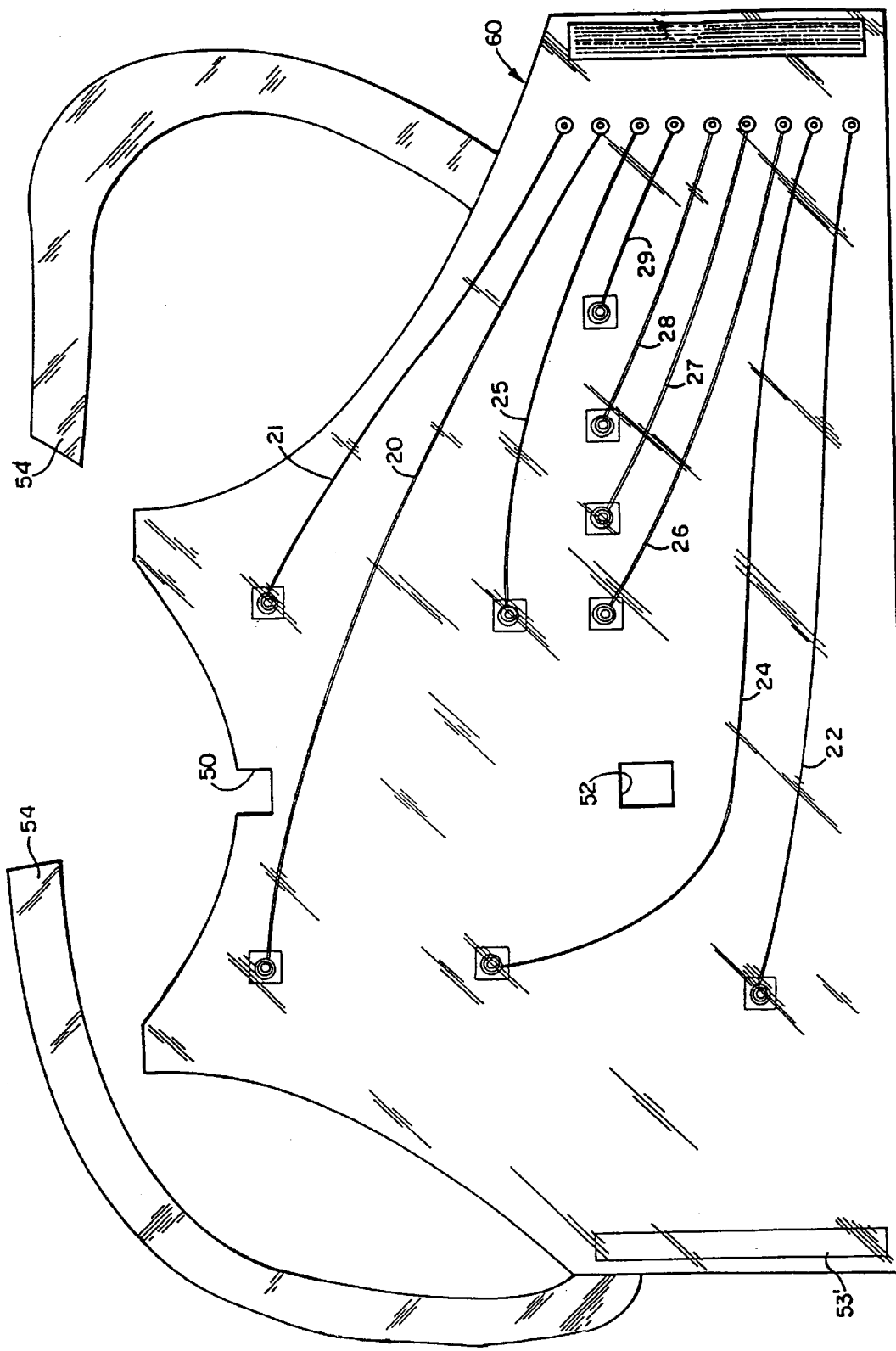
FIG. 4 is a front view of a vest equipped with a plurality of electrodes.

Although the individual receptors, such as the receptor 35 having the conductive adhesive 38 may provide sufficient adhesion for maintaining the bib 10 in position, it is an additional feature of the present invention to provide two or more positioning members for more accurate placement of the bib on a patient's chest. In a preferred embodiment as illustrated in FIG. 3, the positioning members are located for placement over bony portions of the anatomy which are easily recognized. More particularly, in the illustrated embodiment the positioning members are located for placement over the clavicles and sternum, the bony chest landmarks, and include clavicle patches 42 and 43, an upper sternum patch 44, and a lower sternum patch 45. The positioning members or patches 42–45 may include any suitable adhesive applied to the contact surface 11 of the bib 10.

As can now be appreciated, by mounting the strips 20–19 securely to the bib 10 and thus pre-positioning the receptors ends such as end 35, accurate placement for accurate and reproducible test results is greatly facilitated. The positioning patches 42–45 further assure that the bib 10 will remain in place throughout the testing session.

For additional ease in placement, the bib 10 may color-encoded on the visible or non-contacting bib surface for ready recognition of the bony, chest landmarks, and may include, for example a colored portion on the non-contacting surface of the bib 10 as illustrated by hatching shown on the patches 42–45 in FIG. 2. An outline and/or colored markings for each of the clavicles and sternum and/or lead receptors such as outline 50 may also be printed on the non-contacting bib surface for ease in bib placement.

As shown in FIG. 3, a bib 10 may be provided with a slot or notch 60 which positions the upper portion of the bib 10 at the clavicular notch. The slot 52 is then utilized to align the bib 10 with the sternum notch. With the alignment along the clavicular notch and sternum notch the receptor ends then automatically can be repeatedly placed about the chest when the bib 10 is wrapped around the body since the electrodes maintain the same pattern and location. The bib 10 may be tied with belts 54, 54' or a VELCRO® fastener 53, 53'.

The bib 10 can be provided in a range of sizes, for example large, medium and small, to accommodate patients of differing stature. The bib can also be anatomically constructed to provide for women patients. The bib may be formed from any non-conductive flexible natural or synthetic sheet material which is capable of accepting a print, for example, cotton, Mylar, polyolefin (polypropylene, polyethylene), polyvinyl chloride, nylon, and the like or mixtures thereof.

The strips or wires can be of any electrically conductive graphite, polymer or metal, graphite, and the like, for example, N-vinyl pyrrolidone, copper, silver, aluminum, and the like or alloys thereof. The strips can be made of metal foil or made from a conductive paste of the metal in particle form in a suitable binder which is printed or silk screened onto the bib. Alternatively, a single wire or a multiplicity of fine wires may be adhered onto the bib by a non-conductive adhesive in the desired pattern. The conductive polymer may be heat pressed or otherwise adhered to the bib.

If desired, the exposed conductive strips or wires way be partially coated with a coating solution of a non-conductive polymeric material so that only the selective end portions are exposed. Suitable coatings include polyesters, ethylene-vinyl acetate copolymer, polyvinyl chloride and copolymers thereof, ABS, acrylic rubbers, and the like.

The apparatus of the invention has the advantage of being easily manufactured and not requiring the use of conventional electrodes. However, if greater sensitivity is desired, electrodes can be added onto the end strip by any conventional fastening.

Although the invention has been discussed and illustrated as using metallic strips, the invention is not limited to electrically conducting strips, and any technique for incorporating conductive materials in a predetermined pattern into a flexible sheet material can be used. Other modifications can be made without departing from the spirit of the invention, the scope of which is set forth in the following claims.

What is claimed is:

1. An electrodeless apparatus for wearing by a patient about the chest area for transmitting electrical impulses from the patient to an electrocardiograph, consisting essentially of a flexible non-conductive sheet, a plurality of electrically conductive strips or wires mounted on said sheet, each strip or wire having a first end adapted for electrical connection with the skin of the patient for receiving and transmitting electrical impulses, and a second end adapted for connection with a terminal for transmitting electrical impulses to an electrocardiograph device, whereby electrical impulses are transmitted through said strip or wire without an electrode, and wherein each said strip or wire comprises copper, silver, aluminum or alloys thereof.

2. An electrode apparatus according to claim 1, wherein each said strip or wire is printed or silk-screened on said non-conductive sheet.

3. An electrodeless apparatus for wearing by a patient about the chest area for transmitting electrical impulses from the patient to an electrocardiograph, consisting essentially of a flexible non-conductive sheet, a plurality of electrically conductive strips or wires disposed on said sheet, each strip or wire having a first end adapted for electrical connection with the skin of the patient for receiving and transmitting electrical impulses, and a second end adapted for connection with a terminal for transmitting electrical impulses to an electrocardiograph device, whereby electrical impulses are transmitted through said strip or wire without an electrode, and wherein each said strip or wire is comprised of a metallic material.

4. An electrode apparatus according to claim 3, wherein each said strip or wire is printed or silk-screened on said non-conductive sheet.

5. An electrodeless apparatus for wearing by a patient about the chest area for transmitting electrical impulses from the patient to an electrocardiograph, consisting essentially of a flexible non-conductive sheet, a plurality of electrically conductive strips or wires disposed on said sheet, each strip or wire having a first end adapted for electrical connection with the skin of the patient for receiving and transmitting electrical impulses, and a second end adapted for connection with a terminal for transmitting electrical impulses to an electrocardiograph device, whereby electrical impulses are transmitted through said strip or wire without an electrode, and wherein each said strip or wire is comprised of a polymer material.

6. An electrode apparatus according to claim 5, wherein each said strip or wire is heat pressed on said non-conductive sheet.

7. An electrodeless apparatus for wearing by a patient about the chest area for transmitting electrical impulses from the patient to an electrocardiograph, consisting essentially of a flexible non-conductive sheet, a plurality of electrically conductive strips or wires disposed on said sheet, each strip or wire having a first end adapted for electrical connection with the skin of the patient for receiving and transmitting electrical impulses, and a second end adapted for connection with a terminal for transmitting electrical impulses to an electrocardiograph device, whereby electrical impulses are transmitted through said strip or wire without an electrode, and wherein each said strip or wire is comprised of a conductive paste.

8. An electrode apparatus according to claim 7, wherein each said strip or wire is printed or silk-screened on said non-conductive sheet.

\* \* \* \* \*

UNITED STATES PATENT AND TRADEMARK OFFICE
CERTIFICATE OF CORRECTION

PATENT NO. : 5,865,740

DATED : February 2, 1999

INVENTOR(S) : ROBERT J. KELLY, ET AL.

It is certified that error appears in the above-identified patent and that said Letters Patent is hereby corrected as shown below:

COLUMN 2,
Line 16, "aperatures" should read --apertures--;
Line 24, "Bare et al" should read --Bare et al.--; and
Line 60, "professionals" should read --professional--.

COLUMN 4,
Line 2, "patient" should read --patient which--; and
Line 66, "strips 20-19" should read --strips 20-29--.

COLUMN 5,
Line 5, "may" should read --may be--.

COLUMN 6,
Line 13, "electrode" should read --electrodeless--;
Line 29, "electrode" should read --electrodeless--;
Line 45, "electrode" should read --electrodeless--;
Line 46, "heat pressed" should read --printed or silk-screened--; and
Line 61, "electrode" should read --electrodeless--.

Signed and Sealed this

Twenty-first Day of September, 1999

Q. TODD DICKINSON

*Attest:*

*Attesting Officer*     Acting Commissioner of Patents and Trademarks